US012697111B2

(12) United States Patent
Tuttle et al.

(10) Patent No.: US 12,697,111 B2
(45) Date of Patent: Aug. 4, 2026

(54) SOFT TISSUE FIXATION DEVICES AND METHODS

(71) Applicant: Carilion Clinic, Roanoke, VA (US)

(72) Inventors: John R. Tuttle, Roanoke, VA (US); Rob Fippinger, Roanoke, VA (US)

(73) Assignee: Carilion Clinic, Roanoke, VA (US)

( * ) Notice: Subject to any disclaimer, the term of this patent is extended or adjusted under 35 U.S.C. 154(b) by 507 days.

(21) Appl. No.: 17/686,375

(22) Filed: Mar. 3, 2022

(65) Prior Publication Data

US 2022/0280148 A1       Sep. 8, 2022

Related U.S. Application Data

(60) Provisional application No. 63/156,278, filed on Mar. 3, 2021.

(51) Int. Cl.
*A61B 17/04*       (2006.01)
*A61F 2/08*        (2006.01)
*A61F 2/00*        (2006.01)

(52) U.S. Cl.
CPC ........ *A61B 17/0401* (2013.01); *A61F 2/0811* (2013.01); *A61B 2017/0404* (2013.01); *A61B 2017/0412* (2013.01); *A61B 2017/0464* (2013.01); *A61F 2002/0829* (2013.01); *A61F 2002/0852* (2013.01)

(58) Field of Classification Search
CPC .... A61B 2017/0404; A61B 2017/0412; A61B 2017/0414; A61B 17/0401; A61F 2/0811; A61F 2002/0829; A61F 2002/0852
See application file for complete search history.

(56) References Cited

U.S. PATENT DOCUMENTS

| | | | |
|---|---|---|---|
| 5,720,753 A | 2/1998 | Sander et al. | |
| 6,110,207 A * | 8/2000 | Eichhorn | .............. A61F 2/0811 606/232 |
| 10,786,236 B2 | 9/2020 | Clark et al. | |
| 2003/0130694 A1* | 7/2003 | Bojarski | .............. A61F 2/0811 606/228 |
| 2012/0123541 A1* | 5/2012 | Albertorio | ......... A61B 17/0401 606/232 |
| 2014/0296913 A1* | 10/2014 | Orphanos | .......... A61B 17/0401 606/232 |
| 2018/0055623 A1 | 3/2018 | Blacklidge | |

FOREIGN PATENT DOCUMENTS

| | | | | |
|---|---|---|---|---|
| WO | WO-2012047925 A2 * | 4/2012 | ......... | A61B 17/0401 |
| WO | WO-2016049081 A1 * | 3/2016 | ......... | A61B 17/1714 |

* cited by examiner

*Primary Examiner* — Tan-Uyen T Ho
*Assistant Examiner* — Lindsey R. Rivers
(74) *Attorney, Agent, or Firm* — Jeff B. Vockrodt; CM Law

(57) ABSTRACT

A suture button is provided that is adapted for soft tissue fixation. In one aspect, the button includes a textured bottom surface that allows gripping the soft tissue material and distributing the tension that holds the soft tissue to the bone thereby reducing the likelihood the soft tissue tearing.

20 Claims, 8 Drawing Sheets

SOFT TISSUE FIXATION DEVICES AND METHODS

BACKGROUND

This invention relates to a surgical fastener useful for fastening soft tissue, e.g. ligament, to bone.

One existing type of fastener for soft tissue involves an anchor that secures a knotless suture into a bone using a cortical screw structure. The suture is then secured to the ligament which can be held against the bone adjacent the anchor. One type of such device is disclosed in U.S. Pat. No. 10,786,236, entitled "Knotless Anchor" and is shown in FIG. 1. The knotless anchor 100 can include a series of ribs 101 or other externally facing projections that desirably serve to retain the anchor within the bony anatomy in a known manner (and/or which can secure and/or "wedge" the suture in a desired position between the ribs and the surrounding bony anatomy), with a suture recess or grooved section 102 formed into the anchor ribs 101 (which can include a pair of grooves formed in opposing sides of the anchor). The suture can then be used to secure the tendon against the bone and bone anchor.

Another type of fastener uses a tack and a sleeve as disclosed in U.S. Pat. App. Pub. No. 2018/0055623 A1, entitled "Tendon Retention Device." The tack is configured for press-fit or instrument aided reception into the tendon and associated bone to retain the tendon against the associated bone. The sleeve has an internally threaded bore for threaded reception onto a threaded shaft of the tack from the opposing side of the associated bone. The sleeve further has a head with an anti-loosening feature or anti-loosening features such as, but not limited to, tangs and/or cutouts, that engage the associated bone to aid in preventing the sleeve from working loose from the bone and/or unthreading from the tack. Another type of device is disclosed in U.S. Pat. No. 5,720,753, entitled "Orthopedic Fastener."

SUMMARY OF THE INVENTION

In one aspect, the present invention involves a suture button comprising a body having a top surface and a bottom surface, the bottom surface having a textured surface, body further having two or more openings that allow attachment of the suture button using a suture wire. The body may comprise in one aspect two openings, four openings, or more openings as desired. In one aspect, the suture button has a circular shape. The textured surface of the suture button could be a roughened surface, and/or may have a spike shape. In one aspect, the spike shape may include a cone-shaped spike, and the cone tip may be sharp or rounded. In one aspect the plurality of spikes are distributed evenly over the textured surface.

In another aspect according to an embodiment, the suture button has an elevated bridge between the openings. The elevated bridge may include a rounded top portion perpendicular to an imaginary line connecting the center of each opening. The elevated bridge may also have elevated side portions on each end of the elevated bridge, which are elevated compared to the top portion.

In another aspect, the invention relates to a method for securing soft tissue to bone comprising the steps of: (a) securing a suture within the bone; (b) passing the suture through the soft material; and (c) securing a suture button to the suture, wherein the suture button comprises a body having a top surface and a bottom surface, the bottom surface having a textured surface, the body further having two or more openings that allow attachment of the suture button using a suture wire, wherein the securing of the suture compresses the textured surface against the soft tissue. The suture wire may be secured to the bone using a knotless suture anchor, a screw-in suture anchor, or an interference fit suture anchor.

DETAILED DESCRIPTION

Figure 1:
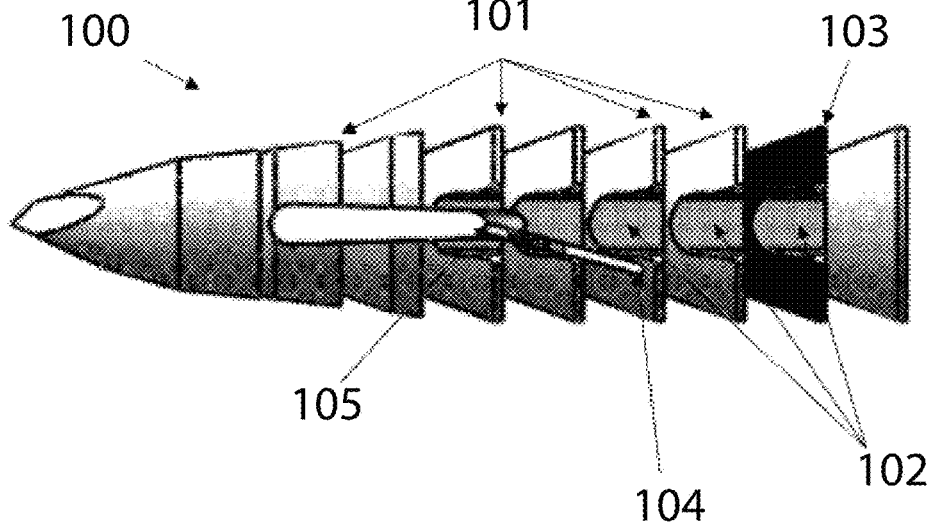
FIG. 1 shows a side plan view of a prior art suture anchor.
Figures 2A, 2B, 2C, 2D, 2E:
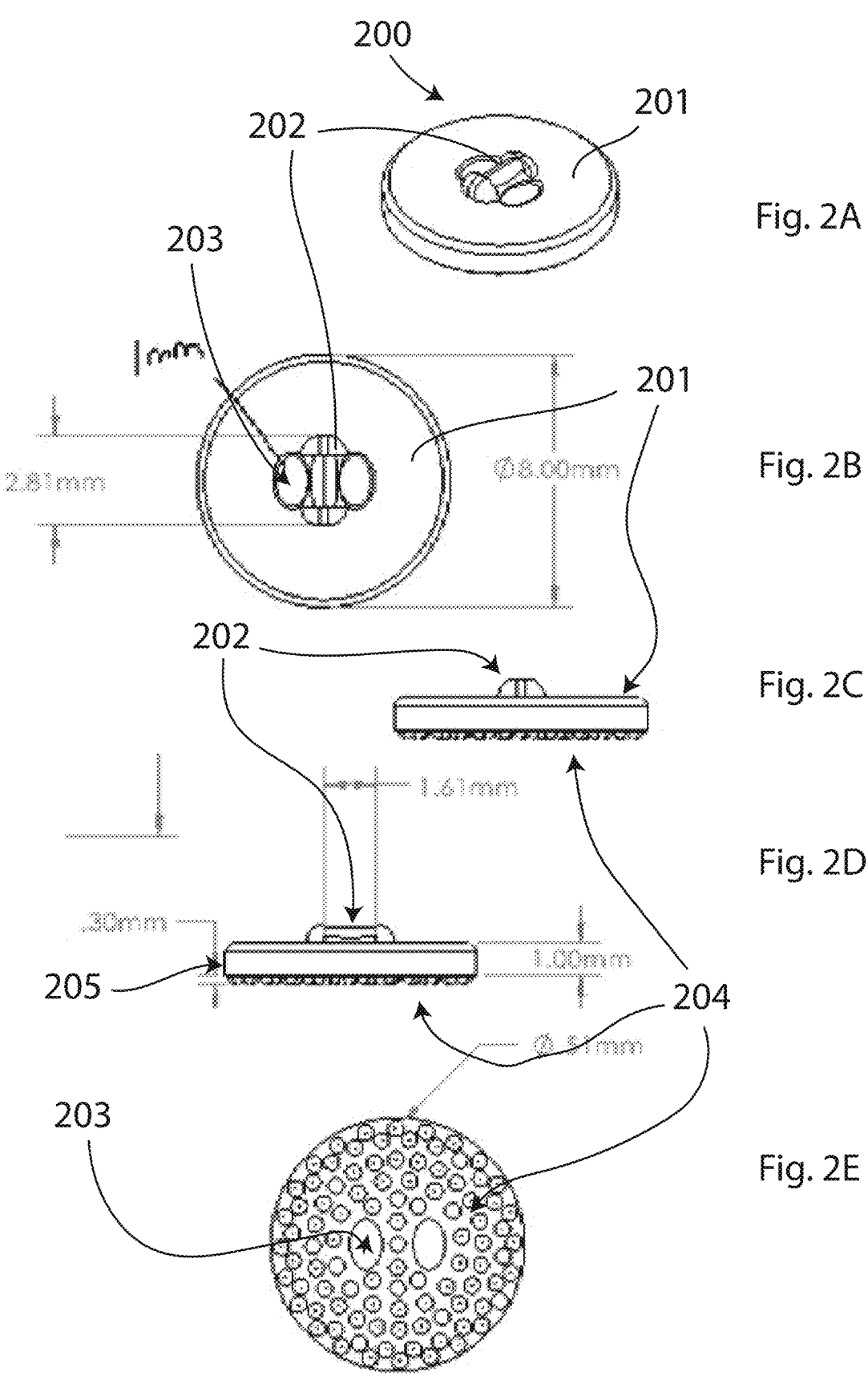
FIG. 2A shows a perspective top view of a suture button of according to an embodiment of the present invention.
FIG. 2B shows a top view of a suture button of according to an embodiment of the present invention.
FIG. 2C shows a first side view of a suture button of according to an embodiment of the present invention.
FIG. 2D shows a second side view of a suture button of according to an embodiment of the present invention.
FIG. 2E shows a bottom view of a suture button of according to an embodiment of the present invention.

The present invention is directed to fixation devices, e.g., soft tissue fixation devices that can fix soft tissue to bone, and methods of making such devices, and methods of using those devices, e.g., surgical techniques for using these devices.

According to one aspect of the invention, the method involves placing a knotless suture anchor through a tendon or soft tissue at the point of desired fixation to bone. This anchor is seated in the bone behind the tissue. A suture button, according to an embodiment of the invention, is then looped into the suture and seated on the top of the tendon or soft tissue securing the tendon or soft tissue to the bone without the need for tying knots, drilling large holes in the bone, etc.

The suture button can be made of a plastic, e.g., PEEK, a fiber reinforced plastic, a biocomposite material, a metal or combinations of different materials. In some examples, the button can include two or more central holes for suture passage with generous material between these holes to exclude the possibility of breakage through this area. The suture buttons are most commonly used in a two-hole configuration but may include four-holes, or any number of holes as desired.

The suture button preferably has a bottom surface that is adapted to engage with the tissue that is to be attached to the bone. The bottom surface of the suture button is preferably textured, and not smooth. In one aspect, the texture of the bottom surface has small, numerous spikes that cover the surface that will not cut the tissue underneath but will provide a high friction interface to improve tissue fixation strength.

The button may be non-porous or can be porous. In one aspect the button can be used with anchors including, for example, fibertak knotless suture anchors.

The invention has several attributes including, but not limited to, decreased OR time/faster procedure, simple, single incision without the need for a cannula, no knot tying, no risk for a soft tissue bridge, all arthroscopic technique (not an open incision), perfect biceps tendon tension is possible, less bone loss, no risk for torsional fracture, may contribute to less pain as well.

No concern with biceps tendon size, i.e. too large for bone tunnel. No concern with biceps tendon tearing from screw placement.

The button itself can be used to compress the tissue to the bone. The anchor (inside the bone), which can be a suture or knotless anchor can connect to the button so the tendon and the bone are between the anchor and the button.

The button can grip into the soft tissue, but does not generally cut into the tissue. The button can interdigitate into the tissue.

The exact shape of the button can vary and includes round, triangular, rectangular or other shapes.

The button can include, or be used, with growth factors including, for example, FGF, BMP-12, -13, -14, CTGF (connective tissue growth factor), IGF-1, PDGF, TGFβ, and VEGF. The button can also be used with adhesive or glues if desired.

The button can be used to repair many different soft tissue injuries including, for example, biceps tendon tears. For example, the long head of the biceps (or other heads of the biceps) can be repaired using the button.

The button could also be used in subscapularous repair after total shoulder; multiligament repair in the knee (MCL) or areas.

In a biceps tendon repair, the button can be used to first fix the biceps tendon to the bone prior to releasing it from the shoulder attachment point. This procedure should maintain the appropriate tension in the biceps.

The button can be used with drill guides, e.g., a forked drill guide, so the button can be adjacent to a suitable area of the soft tissue post-repair.

The button can be present in kit form including one or more of an anchor, instructions, drill bits, drill guides, the button, etc.

FIG. 2A-E shows a perspective top view of a suture button of according to an embodiment of the present invention. The suture button 200 includes a top surface 201. The suture button has a bridge 202 and holes 203. The holes 203 are adapted to engage with a suture. The suture button has a sidewall 205, which may include a tapered or rounded engagement with the top surface 201. The suture button has a textured bottom surface that includes conical spikes 204 for engaging with the underlying tissue.

Figure 3:
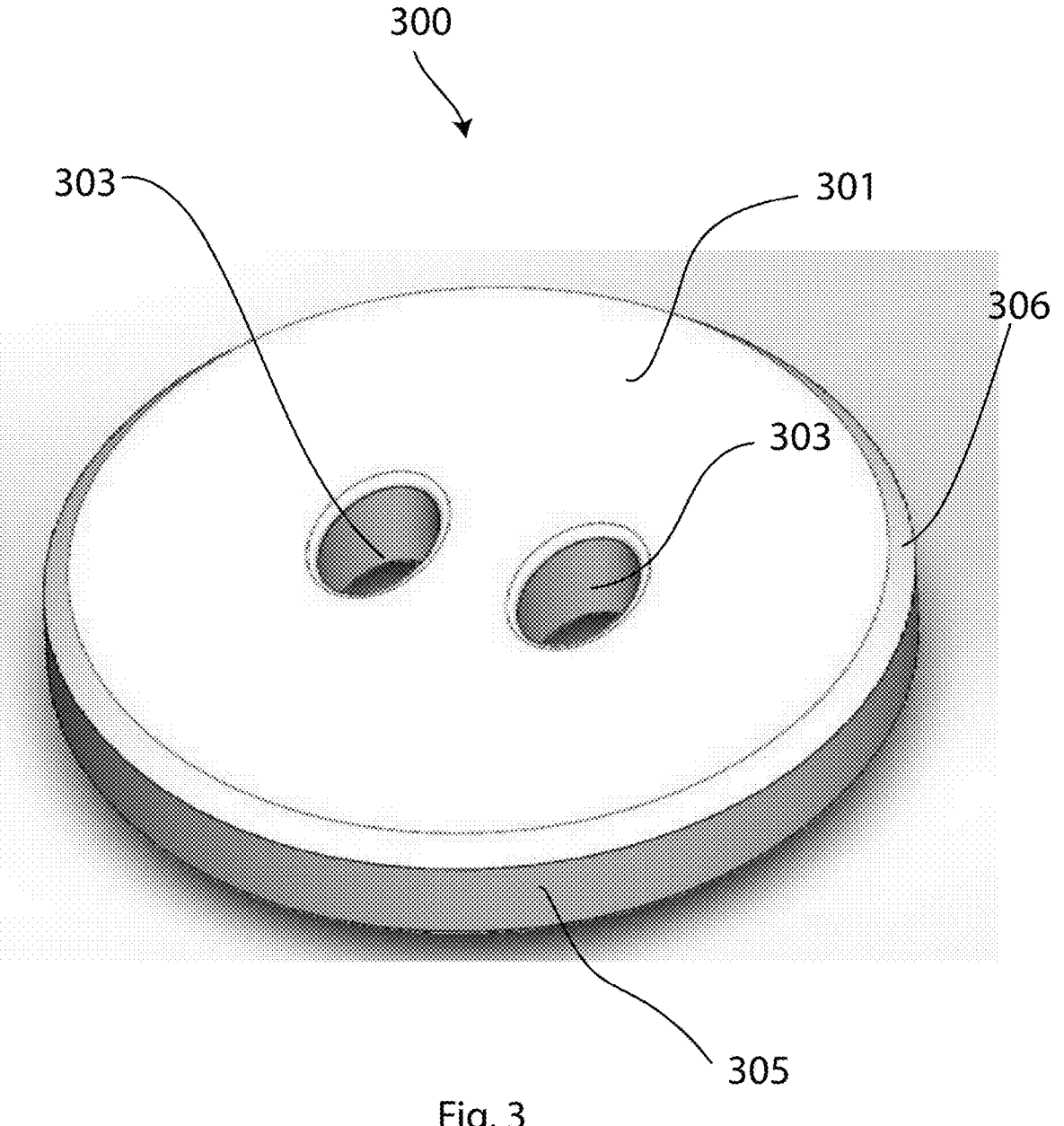
FIG. 3 shows a perspective top view of a suture button according to another embodiment of the present invention.

FIG. 3 shows a perspective top view of a suture button 300 according to another embodiment of the present invention. The suture button 300 has a flat top surface 301 with two holes 303 that are adapted to engage with a suture. The suture button 300 has a sidewall 305, and a tapered surface 306 joining the sidewall 305 with the top surface 301. The under surface (not shown) of the suture button 300 has a textured surface.

Figure 4:
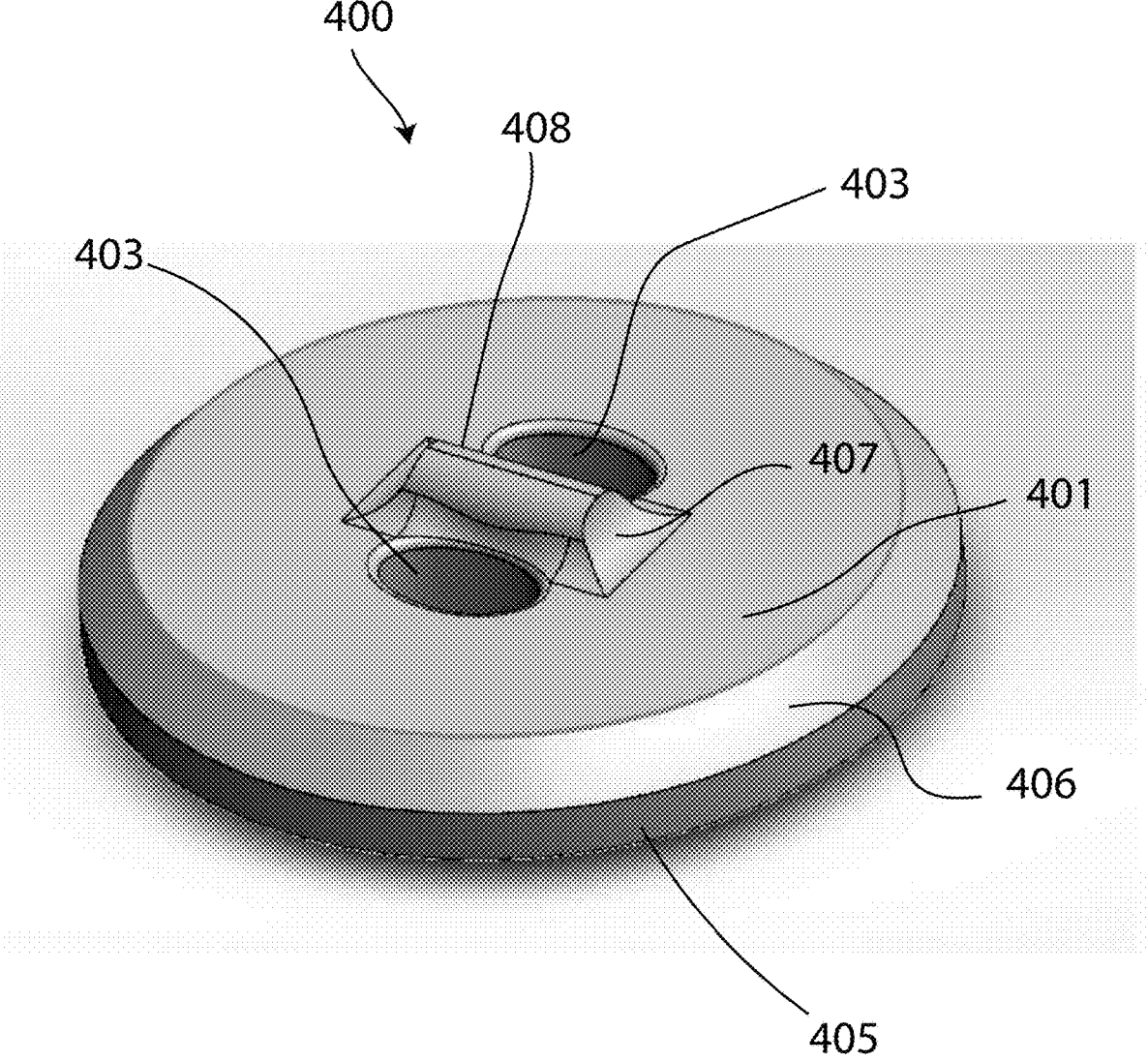
FIG. 4 shows a perspective top view of a suture button according to another embodiment of the present invention.

FIG. 4 shows a perspective top view of a suture button 400 according to another embodiment of the present invention. The suture button 400 has a flat top surface 401 with two holes 403 that are adapted to engage with a suture. The suture button 400 has a sidewall 405, and a tapered surface 406 joining the sidewall 405 with the top surface 401. The under surface (not shown) of the suture button 400 has a textured surface. The suture button include an elevated bridge having a top surface 408 and a side surface 407. The top surface 408 may have a curvature that provides a smooth surface for engagement with the suture material.

Figure 5:
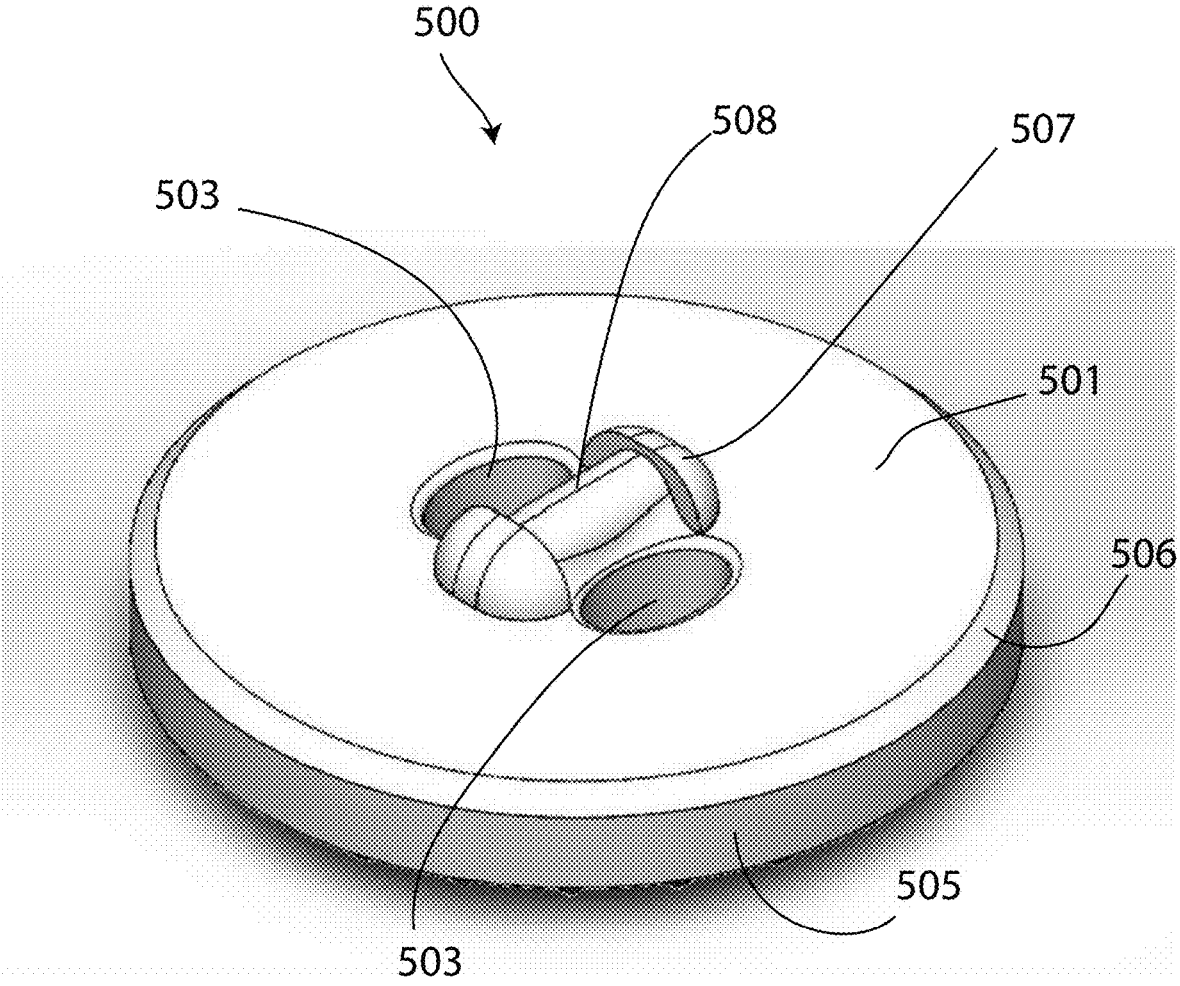
FIG. 5 shows a perspective top view of a suture button according to another embodiment of the present invention.

FIG. 5 shows a perspective top view of a suture button 500 according to another embodiment of the present invention. The suture button 500 has a flat top surface 501 with two holes 503 that are adapted to engage with a suture. The suture button 500 has a sidewall 505, and a tapered surface 506 joining the sidewall 505 with the top surface 501. The under surface (not shown) of the suture button 500 has a textured surface. The suture button include an elevated bridge having a top surface 508 and a side surface 507. The top surface 508 may have a cut-out curvature feature that provides a smooth surface for engagement with the suture material. The smooth top surface 508 of the elevated bridge is cut-out from the sidewall 507 providing a guide for sutures to loop through the holes 503.

Figure 6:
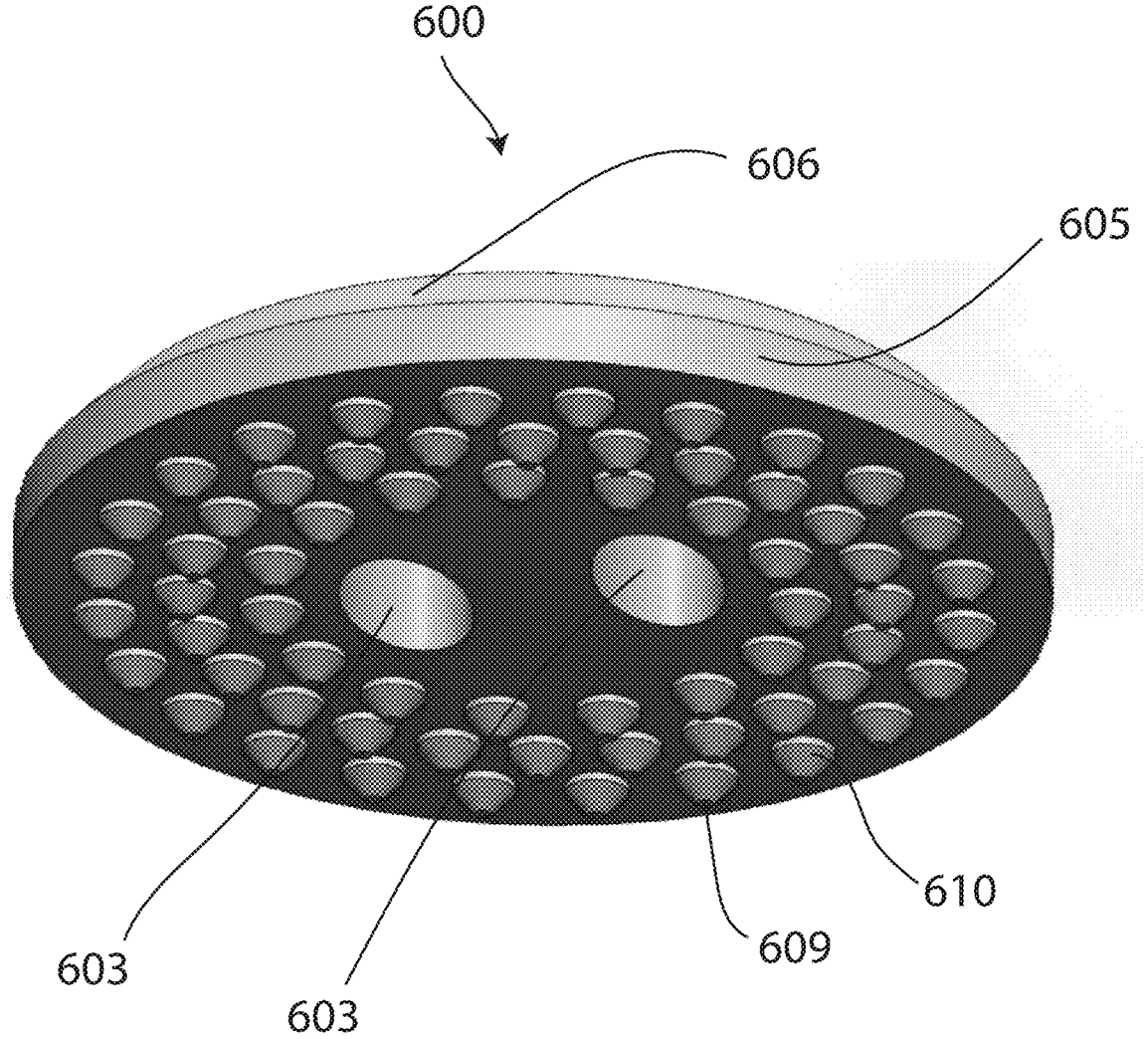
FIG. 6 shows a bottom perspective view of a sure button according to another embodiment of the present invention.

FIG. 6 shows a bottom perspective view of a suture button 600 according to another embodiment of the present invention. The suture button has a sidewall 605 and a tapered surface 606 connecting the sidewall 605 to the top surface (not shown). The holes 603 are shown at the bottom surface. The textured bottom surface has conical spikes that have a rounded point 609 and a tapered sidewall 610.

Figure 7:
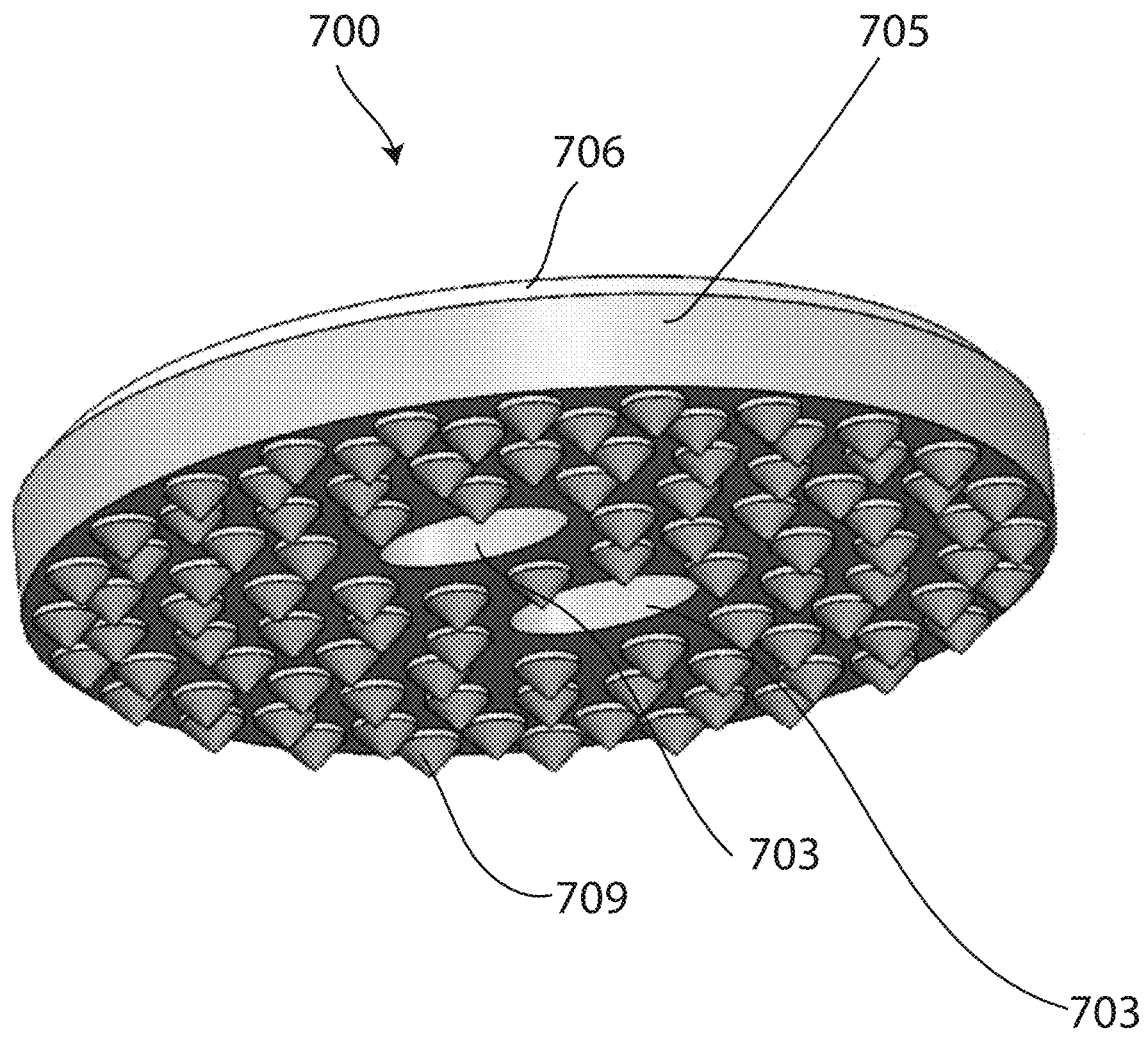
FIG. 7 shows a bottom perspective view of a sure button according to another embodiment of the present invention.

FIG. 7 shows a bottom perspective view of a suture button 700 according to another embodiment of the present invention. The suture button has a sidewall 705 and a tapered surface 706 connecting the sidewall 705 to the top surface (not shown). The holes 703 are shown at the bottom surface. The textured bottom surface has conical spikes that have a sharp point 709.

Figure 8:
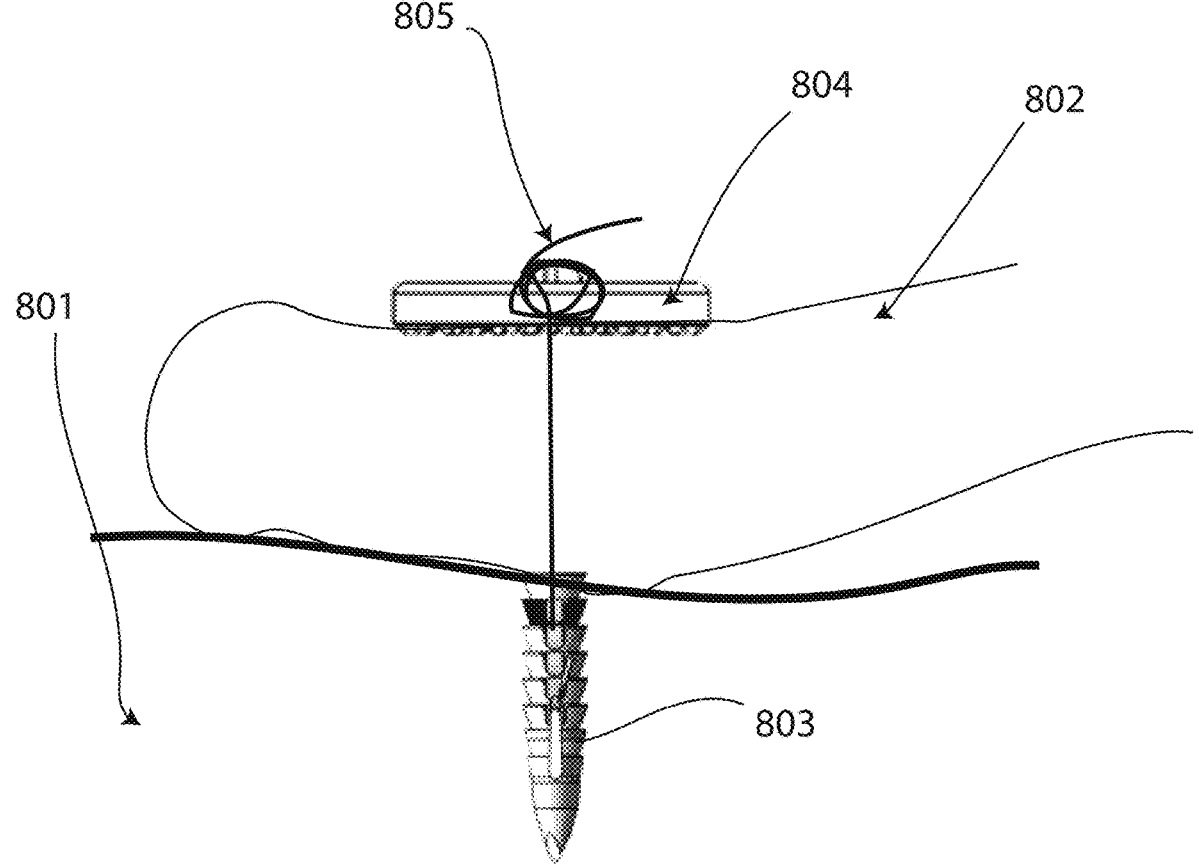
FIG. 8 shows a sure button according to an embodiment of the invention that is used to secure a tendon.

FIG. 8 shows a suture button 804 according to an embodiment of the invention that is used to secure a tendon. The suture button may be any one of the suture buttons described above with respect to FIGS. 2-7. The suture button 804 is attached to a suture wire 805 that extends through the tendon 802 down to underlying bone 801 in which a knotless suture anchor is installed.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims.

What is claimed is:

1. A suture button comprising a body having a planar top surface and a bottom surface, the top surface having an elevated bridge, the bottom surface having a textured surface, the body further having at least a first opening and at least a second opening, the at least first opening and the at least second opening being formed between the planar top surface of the body and the bottom surface of the body and allowing attachment of the suture button using a suture wire, the elevated bridge being positioned between the at least first opening and the at least second opening such that the entire region between the at least first opening and the at least second opening is elevated relative to the planar top surface and a remaining portion of the planar top surface surrounding the at least first opening and the at least second opening being level.

2. The suture button of claim 1, wherein the body defines exactly two openings, including the at least first opening and the at least second opening.

3. The suture button of claim 1, wherein the body comprises four openings, including the at least first opening and the at least second opening.

4. The suture button of claim 1, wherein the body has a circular shape.

5. The suture button of claim 1, wherein the elevated bridge includes an elongated dimension that runs perpendicular to an imaginary line connecting the center of each opening.

6. The suture button of claim 5, wherein the elevated bridge includes a rounded top portion.

7. The suture button of claim 5, wherein the elevated bridge includes elevated side portions on each end of the elongated dimension of the elevated bridge.

8. The suture button of claim 1, wherein the textured surface comprises a plurality of spikes.

9. The suture button of claim 8, wherein the plurality of spikes have a conical shape with either a rounded or sharp tip.

10. The suture button of claim 8, wherein the plurality of spikes are distributed evenly over the textured surface.

11. A method for securing soft tissue to bone comprising the steps of:

> securing a suture within the bone;
> passing the suture through the soft material;
> securing a suture button to the suture, wherein the suture button comprises a body having a planar top surface and a bottom surface, the top surface having an elevated bridge, the bottom surface having a textured surface, the body further having at least a first opening and at least a second opening, the at least first opening and the at least second opening being formed between the planar top surface of the body and the bottom surface of the body and allowing attachment of the suture button using a suture wire, the elevated bridge being positioned between the at least first opening and the at least second opening such that the entire region between the at least first opening and the at least second opening is elevated relative to the planar top surface and a remaining portion of the planar top surface surrounding the at least first opening and the at least second opening being level, wherein the securing of the suture compresses the textured surface against the soft tissue.

12. The method of claim 11, wherein the body defines exactly two openings, including the at least first opening and the at least second opening.

13. The method of claim 11, wherein the body comprises four openings, including the at least first opening and the at least second opening.

14. The method of claim 11, wherein the body has a circular shape.

15. The method of claim 11, wherein the elevated bridge includes an elongated dimension that runs perpendicular to an imaginary line connecting the center of each opening.

16. The method of claim 15, wherein the elevated bridge includes a rounded top portion.

17. The method of claim 15, wherein the elevated bridge includes elevated side portions on each end of the elongated dimension of the elevated bridge.

18. The method of claim 11, wherein the textured surface comprises a plurality of spikes.

19. The method of claim 18, wherein the plurality of spikes have a conical shape with either a rounded or sharp tip.

20. The method of claim 11, wherein the suture wire is secured to the bone using a knotless suture anchor, a screw-in suture anchor, or an interference fit suture anchor.

* * * * *